United States Patent [19]

Detty et al.

[11] Patent Number: 4,525,443

[45] Date of Patent: Jun. 25, 1985

[54] NOVEL 3-TRIHALOCHALCOGENPROPENONE COMPOUNDS

[75] Inventors: Michael R. Detty; Jerome H. Perlstein, both of Rochester, N.Y.

[73] Assignee: Eastman Kodak Company, Rochester, N.Y.

[21] Appl. No.: 542,807

[22] Filed: Oct. 17, 1983

[51] Int. Cl.³ .............................................. G03G 5/09
[52] U.S. Cl. ...................................... 430/83; 260/550
[58] Field of Search ............ 260/239 R, 550; 430/74, 430/83, 900

[56] References Cited

U.S. PATENT DOCUMENTS 4,329,284 5/1982 Detty et al. .

Primary Examiner—John L. Goodrow
Attorney, Agent, or Firm—John R. Everett

[57] ABSTRACT

Novel Z-3-trihalochalcogenpropenone compounds selected from the group consisting of Z-3-trihaloseleniumpropenone and Z-3-trihalotelluriumpropenone and methods of making such compounds are disclosed. The Z-3-trihalochalcogenpropenone compounds are useful as sensitizers in electrophotographic compositions and elements.

12 Claims, No Drawings

NOVEL 3-TRIHALOCHALCOGENPROPENONE COMPOUNDS

FIELD OF THE INVENTION

This invention relates to trihalochalcogenpropenone compounds, methods for making such compounds and electrophotographic compositions and elements comprising sensitizing amounts of such compounds.

BACKGROUND OF THE INVENTION

In photographic compositions, such as electrophotographic compositions, sensitizing compounds are often used to improve the sensitivity of the compositions. A wide variety of such compositions are in use. There exists a continuing effort to improve the performance of currently used compositions.

SUMMARY OF THE INVENTION

The present invention provides a class of Z-3-trihalochalcogenpropenone compounds selected from the group consisting of Z-3-trihaloseleniumpropenone and Z-3-trihalotelluriumpropenone. The compounds are useful in increasing the sensitivity and quantum efficiency of electrophotographic compositions and elements in which one component is an electron donor.

In a preferred embodiment the Z-3-trihalochalcogenpropenone compounds of the invention have the structure

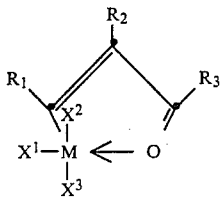

wherein $R_1$ and $R_2$ each independently represents hydrogen, alkyl or aryl; or $R_1$ and $R_2$ taken together with the carbon atoms to which they are attached form a mono- or polycyclic, heterocyclic or aromatic fused ring structure;

$R_3$ represents hydrogen, alkyl or aryl;

M represents selenium or tellurium; and

X individually represents bromide or chloride.

"Alkyl" refers to a branched- or straight-chained hydrocarbon having up to about 20 carbon atoms, such as methyl, butyl, dodecyl, nonyl, isobutyl, neopentyl, etc.; "aryl" includes phenyl, naphthyl and anthryl. Aryl and alkyl may both be substituted by other alkyl groups and other substituents such as nitro, cyano, carboxy, methoxy, amino, dialkylamino, halogen and alkoxy groups. Halogen; refers to chlorine, bromine, fluorine and iodine. Examples of heterocyclic groups include pyridine, thiophene, furan, selenophene, tellurophene, pyran, thiopyran and the like. Examples of aromatic groups include benzene, naphthalene, anthracene and the like.

DETAILS OF THE INVENTION

The Z-3-trihalochalcogenpropenone of our invention are prepared by a novel halogenation method comprising:

Reacting chlorine or bromine with an oxachalcogenolium halide of the structure

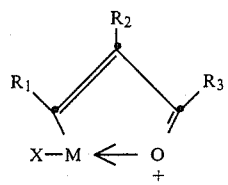

wherein $R_1$, $R_2$, $R_3$, M and X are as previously defined.

The resulting Z-3-trihalochalcogenpropenone is then isolated.

The oxachalcogenolium halide starting materials used in step 1 of the process are prepared by the procedure of U.S. Pat. No. 4,329,284. That procedure involves treating a 3-aryl or 3-alkylchalcogenoacryloyl halide with a Friedel-Crafts catalyst and then isolating the resulting oxochalcogenol-1-ium halide. The disclosure of U.S. Pat. No. 4,329,284 is expressly incorporated herein by reference.

Useful 1,2-oxachalcogenol-1-ium halides include 3-methyl-5-phenyl-1,2-oxatellurol-1-ium chloride, 3-ethyl-5-phenyl-,2-oxatellurol-1-ium chloride, 3-phenyl-5-phenyl-1,2-oxatellurol-1-ium chloride, 3-methyl-5-(p-methoxyphenyl)-1,2-oxatellurol-1-ium chloride, 3-phenyl-5-(p-methoxyphenyl)-1,2-oxatellurol-1-ium chloride, 3-methyl-5-(p-fluorophenyl)-1,2-oxatellurol-1-ium chloride, 3-phenyl-5-(p-fluorophenyl)-1,2-oxatellurol-1-ium chloride and 3-methyl-5-(p-N-N-dimethylaminophenyl)-1,2-oxatellurol-1-ium chloride as well as the corresponding bromides.

Halogenation reactions are well known. General descriptions of such reactions are found in March, "Advanced Organic Chemistry: Reactions, Mechanisms and Structure" McGraw-Hill, New York, 1968.

In general, such halogenation reactions involve dissolving the oxachalcogenol-1-ium halide in a solvent such as acetonitrile, propionitrile, or methylene chloride, cooling the solution to about 0° C., and then adding the halogen to the solution of the oxachalcogenol-1-ium halide as a solution or as a gas.

The Z-3-trihalochalcogenpropenone compounds are isolated from the reaction mixture and purified using any chemical separation method or technique for isolation and purification of chemical compounds. Such methods and techniques include (a) precipitating the product by concentrating the reaction mixture and/or adding ether, or by drowning the crude reaction mixture with cold water;

(b) removing the product by extraction with a water-immiscible solvent such as a halogenated solvent;

(c) drying;

(d) precipitation by concentration and recrystallization from an organic solvent such as acetonitrile when the products are solids; and (e) separating chromatographically when the products are liquids.

The above described method for the preparation of the Z-3-trihalochalcogenpropenone compounds of the invention are illustrated in the following examples.

The present invention provides photoconductive compounds and elements in which electron donating compounds (p-type photoconductors) are combined with sensitizing amounts of the Z-3-trihalochalcogenpropenone.

These compositions and elements are useful in electrophotographic processes. Such processes employ a photoconductive element comprising a support material having thereon a coating containing a photoconductive composition. The element is first given a uniform surface charge after a suitable period of dark adaptation. The element is then exposed to a pattern of actinic radiation which has the effect of differentially reducing the potential of the surface charge in accordance with the relative energy contained in various parts of the radiation pattern. The differential surface charge or electrostatic latent image remaining on the element is then made visible by contacting the surface with a suitable electroscopic marking material (toner).

The marking material, whether contained in an insulating liquid or on a dry carrier, is deposited on the exposed surface in accordance with either the charge pattern or the absence of charge pattern as desired. The deposited marking material is then either permanently fixed to the surface of the sensitive element by known means such as heat, pressure and solvent vapor, or transferred to a second support to which it is similarly fixed.

The electrostatic latent image can be transferred to a second support and developed there.

The photoconductive elements are generally prepared by blending a dispersion or solution of the electron-donor together with an electrically insulating, film-forming resin binder, when necessary or desirable, and coating the composition on a support or forming a self-support layer of the photoconductive composition. A sensitizing amount of the Z-3-trihalochalcogenpropenone compound is mixed with the donor composition so that, after thorough mixing and drying, the Z-3-trihalochalcogenpropenone compound is uniformly distributed throughout a layer formed from the composition.

The amount of sensitizer which can be added to a photoconductive composition layer to give effective increases in sensitivity can vary widely. The optimum concentration in any given case will vary with the specific donor and specific compound of the invention. Preferred compositions comprise from 0.1 to 10 weight percent of the trihalochalcogenpropenone and 10 to 40 weight percent of the electron donor.

The trihalochalcogenpropenones of the invention are also useful in so-called multi-active photoconductive elements. Such elements have at least two layers comprising an organic electron donating, charge-transport layer in electrical contact with a charge-generation layer comprising the trihalochalcogenpropenone. Both the charge-generation layer and the charge-transport layer may include a binder. The charge-transport layer contains, as the active charge-transport material, one or more organic electron donors capable of accepting and transporting charge carriers generated by the charge-generation layer.

Such multi-active elements are well known in the electrophotographic art and thus need not be discussed in detail here. Berwick et al.'s U.S. Pat. No. 4,175,960 issued Nov. 27, 1979 describes in detail an especially useful arrangement for multi-active elements. The disclosure of Berwick et al. is expressly incorporated herein by reference.

The Z-3-trihalochalcogenpropenone compounds are effective for enhancing the photosensitivity of a wide variety of electron-donating photoconductors. Useful electron donors include:

1. arylamine photoconductors including substituted and unsubstituted arylamines, diarylamines, nonpolymeric triarylamines and polymeric triarylamines such as those described in U.S. Pat. Nos. 3,240,597 by Fox, issued Mar. 15, 1966 and 3,180,730 by Klupfel et al., issued Apr. 27, 1965;

2. polyarylalkane photoconductors of the types described in U.S. Pat. Nos. 3,274,000 by Noe et al., issued Sept. 20, 1966; 3,542,547 by Wilson, issued Nov. 24, 1970 and 3,542,544 by Seus et al., issued Nov. 24, 1970;

3. 3-diarylamino-substituted chalcones of the types described by Fox, U.S. Pat. No. 3,526,501 issued Sept. 1, 1970;

4. nonionic cycloheptenyl compounds of the types described by Looker, U.S. Pat. No. 3,533,786 issued Oct. 13, 1970;

5. compounds containing an: $>$N—N$<$ nucleus, as described by Fox, U.S. Pat. No. 3,542,546 issued Nov. 24, 1970;

6. organic compounds having a 3,3'-bisaryl-2-pyrazoline nucleus, as described by Fox et al., U.S. Pat. No. 3,527,602 issued Sept. 8, 1970;

7. triarylamines in which at least one of the aryl radicals is substituted by either a vinyl radical or a vinylene radical having at least one active hydrogen-containing group, as described by Brantly et al., U.S. Pat. No. 3,567,450 issued Mar. 2, 1971;

8. triarylamines in which at least one of the aryl radicals is substituted by an active hydrogen-containing group, as described by Brantly et al., Belgian Pat. No. 728,563 dated Apr. 30, 1971;

9. any other organic electron donor compound which exhibits photoconductive properties such as those set forth in Australian Patent No. 248,402 and the various polymeric photoconductors such as the photoconductive carbazole polymers described in U.S. Pat. No. 3,421,891, issued Jan. 14, 1969.

EXAMPLE 1

Preparation of
Z-1,3-diphenyl-3-trichlorotelluriumpropenone (1)

A solution of 1.00 g (2.7 mmol) of 3,5-diphenyl-1,2-oxatellurol-1-ium chloride in 10 mL of methylene chloride was chilled to 0° C. and chlorine gas was bubbled into the solution until the initial gold color faded to a pale yellow. The reaction mixture was concentrated and the residue recrystallized from acetonitrile to give 0.79 g of bright yellow needles having a melting point of 166°–168° C.

EXAMPLE 2

Preparation of
Z-1,3-Diphenyl-3-tribromotelluriumpropenone (2)

A solution of 0.42 g (1.0 mmol) of 3,5-diphenyl-1,2-oxatellurol-1-ium bromide in 10 mL of methylene chloride was chilled to 0° C. A solution of 0.19 g (1.2 mmol) of bromine in 2.5 mL of methylene chloride was added, providing a pale yellow solution. The reaction mixture was concentrated and the residue crystallized from acetonitrile to give 0.51 g of 2 as orange crystals having a melting point of 161°–162.5° C.

Table I presents representative Z-3-trihalochalcogenpropenone compounds made according to the described halogenation method. The structure of each compound of the table was confirmed by NMR analysis, infrared spectral analysis, mass spectral analysis and elemental analysis. In the table, φ represents phenyl.

TABLE I

Physical and Spectral Properties of Z—3-Trihalotelluriumpropenones and a Z—3-Trihaloseleniumpropenone

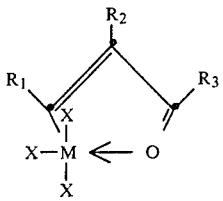

| Cpd. | M | X | R₁ | R₂ | R₃ | mp °C. |
|---|---|---|---|---|---|---|
| 1 | Te | Cl | —φ | H | —φ | 166–168° |
| 2 | Te | Br | —φ | H | —φ | 161–162.5° |
| 3 | Te | Cl | —CH₃ | H | —⌬—N(CH₃)₂ | 162–162.5° |
| 4 | Te | Cl | —CH₃ | H | —φ | 139–141° |
| 5 | Te | Br | —CH₃ | H | —φ | 144–145.5° |
| 6 | Te | Cl | —CH₃ | H | —⌬—F | 152–154° |
| 7 | Te | Cl | —φ | H | —⌬—F | 150–151° |
| 8 | Te | Cl | —H | H | —φ | 96–98° |
| 9 | Te | Br | —H | H | —φ | 115.5–117° |
| 10 | Se | Cl | —CH₃ | H | —⌬—OCH₃ | 127–129° |
| 11* | Te | Cl | —(CH₂)₄— | | —φ | >100° (dec) |
| 12* | Te | Br | —(CH₂)₄— | | —φ | >100° (dec) |

Other compounds which can be made by the method of the invention include

| Cpd. | M | X | R₁ | R₂ | R₃ |
|---|---|---|---|---|---|
| 13 | Te | Cl | (naphthyl) | —φ | H |
| 14 | Te | Cl | (pyridyl-N) | —φ | H |

*In these compounds R₁ and R₂ combine to join a fused ring structure.

The following examples illustrate the use of Z-3-trihalochalcogenpropenones as sensitizers in electrophotographic compositions and elements containing electron donating photoconductors.

EXAMPLES 3–9

An electrophotographic element was prepared by first dissolving sufficient quantities of the trihalochalcogenpropenone and tri-p-tolylamine (electron donor) in dichloromethane (DCM) to provide a dried layer containing 2.0% by weight of the selected Z-3-trihalochalcogenpropenone and 30% by weight of the tri-p-tolylamine. A sufficient amount of a stock solution containing Lexan 145 TM polycarbonate (General Electric) in DCM was added to the solution to obtain a dried layer comprising about 68% by weight of Lexan 145 TM. The solution was stirred for several minutes and then coated at 0.006 mil (0.015 mm) wet thickness on a poly(ethylene terephthalate) support containing 0.4 OD evaporated nickel. After initial evaporation of the solvent, the elements were dried 24 hours in air at 60° C. Dry thickness was about 7 μm.

The quantum efficiency of each element was measured as follows. Samples were corona-charged to a surface potential equivalent to the field strengths, $E_o$, indicated in Table II. They were then exposed to monochromatic radiation at λ=350 nm with a bandwidth of 10 nm. The incident photon flux (I) at 350 nm was measured with an Optronics Laboratories Model 730-A Radiometer. Films were allowed to discharge while exposed to the 350 nm radiation. The initial quantum efficiency $\phi_o$, (the number of electron-hole pairs produced per incident photon) at field strength $E_o$ was then determined from the relation:

$$\phi_o = \frac{\kappa \epsilon_o}{eId} \cdot \frac{dV}{dt}$$

wherein
  κ is the film dielectric constant of 3,
  $\epsilon_o$ is the permitivity of free space constant $8.85419 \times 10^{-12}$ coulombs²/Newton Meters²
  e is the electronic charge constant $1.6022 \times 10^{-19}$ coulombs,
  I is the incident photon flux,
  d is the thickness of the film in meters, and $$\frac{dV}{dt}$$

is the slope of the discharge curve at $E_o$.

The photodischarge sensitivity at 350 nm, $S_{1/2}$, was also determined by allowing the elements to discharge from $E_o$ to $E_o/2$. The amount of radiation necessary to produce this discharge was then calculated from the time required for this half-decay and the incident photon flux.

Table II shows the quantum efficiencies ($\phi_o$) at $E_o$ and photosensitivity ($S_{1/2}$) for seven different electrophotographic elements. The table shows that trihalochalcogenpropenones increase the initial quantum efficiency and/or the photosensitivity of the elements compared to a control element which did not contain a Z-3-trihalochalcogenpropenone.

TABLE II

Initial Quantum Efficiency, $\phi_0$, and Photosensitivity, $S_{\frac{1}{2}}$ for Tri-p-Tolylamine-Lexan 145 Films Containing Z—3-Trihalotelluriumpropenone or Z—3-Trihaloseleniumpropenone Acceptors

| Example No. | Table I Compound | λ, nm | $E_0$, V/cm | $\phi_0$ | $S_{\frac{1}{2}}$, ergs/cm² |
|---|---|---|---|---|---|
| Control | Control | 350 | 1.6 × 10⁶ | 0.0094 | 1500 |
| 3 | 1 | 300 | 7.1 × 10⁵ | 0.109 | 39.4 |
| 4 | 2 | 300 | 2.0 × 10⁵ | 0.0253 | 50.1 |
| 5 | 3 | 300 | 1.0 × 10⁶ | 0.172 | 39.1 |
| 6 | 4 | 300 | 2.8 × 10⁵ | 0.0308 | 50.8 |
| 7 | 5 | 300 | 4.3 × 10⁵ | 0.069 | 35.8 |
| 8 | 6 | 300 | 7.2 × 10⁵ | 0.124 | 32.7 |

TABLE II-continued

Initial Quantum Efficiency, $\phi_0$, and Photosensitivity, $S_{\frac{1}{2}}$ for Tri-p-Tolylamine-Lexan 145 Films Containing Z—3-Trihalotellurium-propenone or Z—3-Trihaloseleniumpropenone Acceptors

| Example No. | Table I Compound | λ, nm | $E_0$, V/cm | $\phi_0$ | $S_{\frac{1}{2}}$, ergs/cm² |
|---|---|---|---|---|---|
| 9 | 7 | 300 | $7.2 \times 10^5$ | 0.126 | 33.6 |

The invention has been described in detail with particular reference to preferred embodiments thereof, but it will be understood that variations and modifications can be effected within the spirit and scope of the invention.

We claim:

1. A Z-3-trihalochalcogenpropenone selected from the group consisting of Z-3-trihaloseleniumpropenone and Z-3-trihalotelluriumpropenone.

2. The compound of claim 1 having the structure:

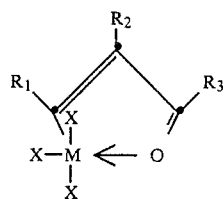

wherein
$R_1$ and $R_2$ each independently represents hydrogen, alkyl or aryl; or $R_1$ and $R_2$ taken together with the carbon atoms to which they are attached form a mono- or polycyclic, heterocyclic or aromatic fused ring structure; and
$R_3$ represents hydrogen, alkyl or aryl;
M represents selenium or tellurium; and
X individually represents bromide or chloride.

3. The compound of claim 2 wherein $R_1$, $R_2$ and $R_3$ each independently represents hydrogen, phenyl, methyl, dimethylaminophenyl, fluorophenyl and methoxyphenyl.

4. The compound of claim 2 selected from Table I.

5. An electrophotographic composition comprising an electron donating organic photoconductor and a sensitizing amount of a Z-3-trihalochalcogenpropenone selected from the group consisting of Z-3-trihalotelluriumpropenone and Z-3-trihaloseleniumpropenone.

6. The composition of claim 5 wherein the Z-3-trihalochalcogenpropenone has the structure

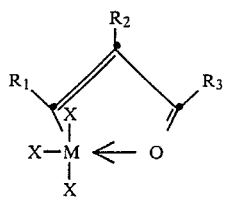

wherein
$R_1$ and $R_2$ each independently represents hydrogen, alkyl or aryl; or $R_1$ and $R_2$ taken together with the carbon atoms to which they are attached form a mono- or polycyclic, heterocyclic or aromatic fused ring structure;
$R_3$ represents hydrogen, alkyl or aryl;
M represents selenium or tellurium; and
X represents bromide or chloride.

7. The composition of claim 6 wherein $R_1$, $R_2$ and $R_3$ each independently represents hydrogen, phenyl, methyl, dimethylaminophenyl, fluorophenyl and methoxyphenyl.

8. The composition of claim 5 wherein the Z-3-trihalochalcogenpropenone is selected from Table I.

9. An electrophotographic element comprising a conductive support and a layer of an electrophotographic composition characterized in that the composition comprises an electron donating organic photoconductor and a sensitizing amount of a Z-3-trihalochalcogenpropenone selected from the group consisting of Z-3-trihalotelluriumpropenone and Z-3-trihaloseleniumpropenone.

10. The element of claim 9 wherein the Z-3-trihalochalcogenpropenone has the structure

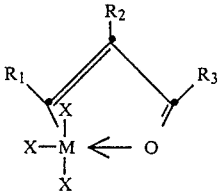

wherein
$R_1$ and $R_2$ each independently represents hydrogen, alkyl or aryl; or $R_1$ and $R_2$ taken together with the carbon atoms to which they are attached form a mono- or polycyclic, heterocyclic or aromatic fused ring structure;
$R_3$ represents hydrogen, alkyl or aryl;
M represents selenium or tellurium; and
X represents bromide or chloride.

11. The element of claim 10 wherein $R_1$, $R_2$ and $R_3$ each independently represents hydrogen, phenyl, methyl, dimethylaminophenyl, fluorophenyl and methoxyphenyl.

12. The element of claim 10 wherein the Z-3-trihalochalcogenpropenone is selected from Table I.

* * * * *